United States Patent
Suda et al.

(10) Patent No.: US 8,027,101 B2
(45) Date of Patent: Sep. 27, 2011

(54) OPTICAL ELEMENT FIXING COMPONENT AND IMAGING UNIT

(75) Inventors: Nobuyuki Suda, Sagamihara (JP); Yukichi Hanayama, Tokyo (JP); Masamichi Hijino, Uenohara (JP)

(73) Assignee: Olympus Corporation, Tokyo (JP)

( * ) Notice: Subject to any disclaimer, the term of this patent is extended or adjusted under 35 U.S.C. 154(b) by 0 days.

(21) Appl. No.: 12/777,612

(22) Filed: May 11, 2010

(65) Prior Publication Data

US 2010/0214676 A1    Aug. 26, 2010

Related U.S. Application Data

(63) Continuation of application No. PCT/JP2008/070481, filed on Nov. 11, 2008.

(30) Foreign Application Priority Data

Nov. 12, 2007  (JP) ................................. 2007-293126
Jan. 21, 2008  (JP) ................................. 2008-010324

(51) Int. Cl.
*G02B 7/02* (2006.01)
(52) U.S. Cl. ........................................ 359/811; 359/819
(58) Field of Classification Search .................. 359/811, 359/813, 814, 815, 819, 818
See application file for complete search history.

(56) References Cited

U.S. PATENT DOCUMENTS

| | | | |
|---|---|---|---|
| 3,599,630 A * | 8/1971 | Sato et al. ...................... 600/109 |
| 2002/0079430 A1* | 6/2002 | Rossi ............................ 250/216 |
| 2003/0232260 A1* | 12/2003 | Irving et al. .................... 430/21 |
| 2008/0101431 A1* | 5/2008 | Nishida ........................... 372/66 |

FOREIGN PATENT DOCUMENTS

| | | |
|---|---|---|
| JP | 5-131279 A | 5/1993 |
| JP | 6-38901 U | 5/1994 |
| JP | 9-323174 A | 12/1997 |
| JP | 2000-121962 A | 4/2000 |
| JP | 2004-147032 A | 5/2004 |
| JP | 2004-148525 A | 5/2004 |
| JP | 2005-234239 A | 9/2005 |
| JP | 2006-075341 A | 3/2006 |
| JP | 2006-122498 A | 5/2006 |
| JP | 2007-140401 A | 6/2007 |

OTHER PUBLICATIONS

Kovar Technical Data, Dec. 19, 2010.*
Borosilicate glass, Dec. 19, 2010, Wikipedia.*
International Search Report issued for PCT/JP2008/070481, mail date Jan. 27, 2009.

* cited by examiner

*Primary Examiner* — Alicia M Harrington
(74) *Attorney, Agent, or Firm* — Dickstein Shapiro LLP (57) ABSTRACT

The present invention relates to an optical element fixing component having a hollow portion which includes an optical element. The optical element fixing component is made from a non-crystalline alloy, and a ratio of a linear expansion coefficient of the optical element fixing component toward a linear expansion coefficient of the optical element is 1.5 or less.

11 Claims, 6 Drawing Sheets

OPTICAL ELEMENT FIXING COMPONENT AND IMAGING UNIT

CROSS REFERENCE TO RELATED APPLICATIONS

This application is a continuation of International Application No. PCT/JP2008/070481, filed Nov. 11, 2008, which claims priority to Japanese Patent Application No. 2007-293126, filed Nov. 12, 2007, and Japanese Patent Application No. 2008-10324, filed Jan. 21, 2008. The contents of both the PCT Application and the Japanese Applications are incorporated herein by reference.

BACKGROUND OF THE INVENTION

1. Field of the Invention

The present invention relates to an optical element fixing component and an imaging unit.

2. Description of Related Art

In general, an optical element used in an optical device such as an endoscope or a camera is fixed to the device by a lens barrel. In the past, the lens barrel used to fix the optical element was manufactured by using a resin or metal material.

A lens barrel using the resin material is manufactured through injection molding due to the satisfactory moldability of the resin, and has characteristics such that the productivity thereof is excellent compared with a lens barrel obtained by using a metal material. As a lens barrel using the resin material, for example, there is known an endoscope lens barrel shown in Japanese Patent Application, Publication No. 2006-122498.

The lens barrel using the metal material is manufactured through cutting or die-casting, and has characteristics such that the strength and durability thereof are excellent compared with a lens barrel using the resin material. As a lens barrel using the metal material, for example, there is known an endoscope lens barrel shown in Japanese Patent Application, Publication No. 2006-075341.

In addition, as a lens barrel using the resin or metal material, for example, there are known camera lens barrels shown in Japanese Patent Application, Publication Nos. 2004-148525 and 2007-140401. Meanwhile, as methods of bonding the optical element to the lens barrel, there are known bonding through solder (refer to Japanese Patent Application, Publication No. 2007-140401), bonding through thermal caulking (refer to Japanese Patent Application, Publication No. 2004-147032), and bonding through adhesive.

SUMMARY OF THE INVENTION

An object of the present invention is to provide an optical element fixing component which is provided in the front end of an imaging unit and has excellent strength, durability, corrosion resistance, accuracy of dimension, shape stability, and productivity, and an imaging unit which uses the optical element fixing component.

In order to achieve the above-described object, the present invention adopts the following configuration.

(1) An optical element fixing component having a hollow portion in which an optical element is provided therein, wherein the optical element fixing component is made from a non-crystalline alloy, and a ratio of a linear expansion coefficient of the optical element fixing component toward a linear expansion coefficient of the optical element is 1.5 or less.

In the optical element fixing component according to (1), it is preferable that the ratio is 1.0 or more.

In the optical element fixing component according to (1), it is preferable that the linear expansion coefficient of the non-crystalline alloy is $15 \times 10^{-6}/°$ C. or less.

In the optical element fixing component according to (1), it is preferable that a glass transition area of the non-crystalline alloy is 20° C. or more.

In the optical element fixing component according to (1), it is preferable that the non-crystalline alloy is a Zr-based alloy.

(2) An imaging unit comprising the optical element fixing component according to (1); and an optical element which is fixed to a hollow portion of the optical element fixing component.

The imaging unit according to (2) may further comprising a protection cover which is made from a non-crystalline alloy.

The imaging unit according to (2) may further comprising a bonding layer formed by a melted bonding material provided between the optical element fixing component and the optical element. Furthermore, it is preferable that a melting temperature of the bonding material is lower than a glass transition temperature of the non-crystalline alloy.

(3) An endoscope apparatus or a camera comprising the imaging unit according to (2).

DETAILED DESCRIPTION OF THE INVENTION

As an optical element fixing component of the present invention, for example, a lens barrel provided in the front end of an imaging unit of an optical device such as an endoscope and a camera so as to fix an optical element may be exemplified. As the optical element, for example, a glass lens, a plastic lens, a CCD, a CMOS, and an optical fiber may be exemplified. Here, the imaging unit includes the lens barrel, the optical element fixed to the lens barrel, and other components (wires, protection covers, screws, packings, and the like) assembled in accordance with the necessity.

Hereinafter, the optical element fixing component and the imaging unit of the present invention will be described with reference to the first and second embodiments.

First Embodiment

An endoscope lens barrel 10 as a first embodiment according to the present invention is provided in the front end of an imaging unit 30 to be described later. The endoscope lens barrel 10 has a shape shown in FIGS. 1A and 1B, and a configuration in which a lens barrel fixing screw hole 11, a groove 15, an illumination hole 12, an imaging hole 16, and a treatment tool communication hole 17 are provided at predetermined positions thereof.

Figure 1A:
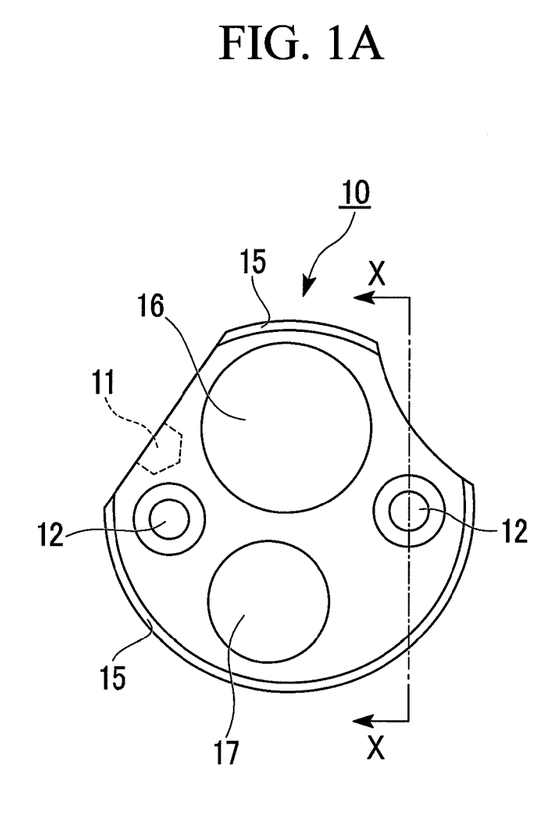
FIG. 1A is a front view showing an endoscope lens barrel according to a first embodiment of the present invention.
Figure 1B:
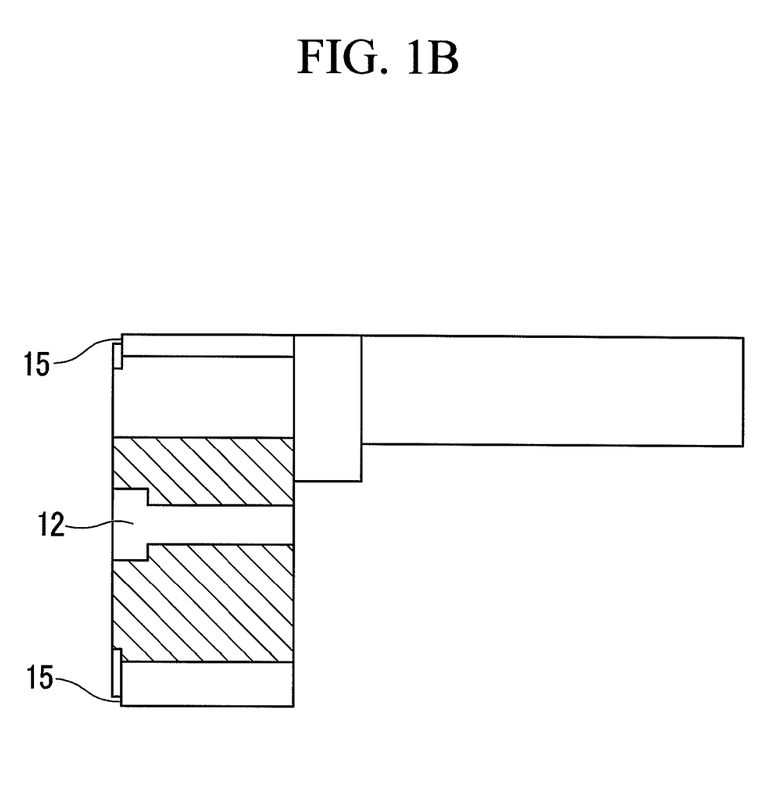
FIG. 1B is a sectional view taken along the line X-X of FIG. 1A and showing the endoscope lens barrel according to the first embodiment of the present invention.

An illumination optical element such as an optical fiber and an illumination lens is fixed to the illumination hole 12. In addition, an imaging optical element such as an object lens and an imaging element such as a CCD are fixed to the imaging hole 16. The treatment tool communication hole 17 is a hole which is used for communication with a treatment tool such as a clamp.

The endoscope lens barrel 10 is made from a zirconium (Zr)-based alloy (a composition: $Zr_{55}Cu_{30}Al_{10}Ni_5$, a crystallization temperature: about 490° C., a glass transition temperature: about 400° C., and a glass transition area: about 90° C.), which is classified as metal glass among non-crystalline alloys.

Here, the non-crystalline alloy is an alloy in which a plurality of metal elements is solidified (amorphoused) without forming a crystalline structure. The non-crystalline alloy is formed by rapidly cooling molten metal raw materials including the plurality of metal elements until the temperature thereof is a glass transition temperature or less. Since the non-crystalline alloy does not have a crystal grain boundary of general crystalline metal, and does not cause grain-boundary corrosion (a phenomenon in which the corrosion occurs in accordance with the crystal grain boundary) resulting from the crystal grain boundary, the non-crystalline alloy has excellent corrosion resistance.

The metal glass is a non-crystalline alloy that has a glass transition area (a value obtained by subtracting the glass transition temperature from the crystallization temperature) of 20° C. or more. Since the metal glass does not cause solidification shrinkage differently from the crystalline metal, the metal glass has highly precise transferability with respect to a mold, and can be used for injection molding. Accordingly, the degree of freedom of the shape, the accuracy of dimension, and the productivity of the molded product are excellent. In addition, properties of the metal glass are low Young's modulus/high strength, and low expansion with respect to heat.

As the metal glass, a Zr-based alloy, Fe-based alloy, Ti-based alloy, Mg-based alloy, and the like may be exemplified. Among them, the Zr-based alloy has particularly excellent low expansion and high accuracy of dimension.

Next, a method of manufacturing the endoscope lens barrel 10 will be described.

The endoscope lens barrel 10 according to the embodiment is manufactured in such a manner that a rough product of the endoscope lens barrel (molded product) 10 is manufactured by using a Zr-based alloy as a metal material in accordance with injection molding, and the rough product is subjected to a secondary process. In addition, it is desirable that the metal material used in the present invention satisfy the following three conditions.

(I) The metal material includes three types or more of metal elements.

(II) The metal material has 12% or more of the three types or more of metal elements having different atom diameters. For example, 12% or more of three types (large, middle, and small) or more of metal elements having different atomic diameters.

(III) The metal material has respective elements that are easily combined. That is, the respective metal elements have attracting properties.

When the metal material satisfies the conditions (I) to (III), it is easy to obtain a molded product which is made from a non-crystalline alloy (metal glass) having a glass transition area of 20° C. or more in accordance with the following manufacturing method.

In the case of using the metal material of the non-crystalline alloy having a glass transition area less than 20° C., since a cooling speck occurs in the molten metal in the process of rapidly cooling the metal material to be described later, crystallization of the molten metal easily occurs. For this reason, it is difficult to obtain a uniform non-crystalline molded product.

Figure 2:
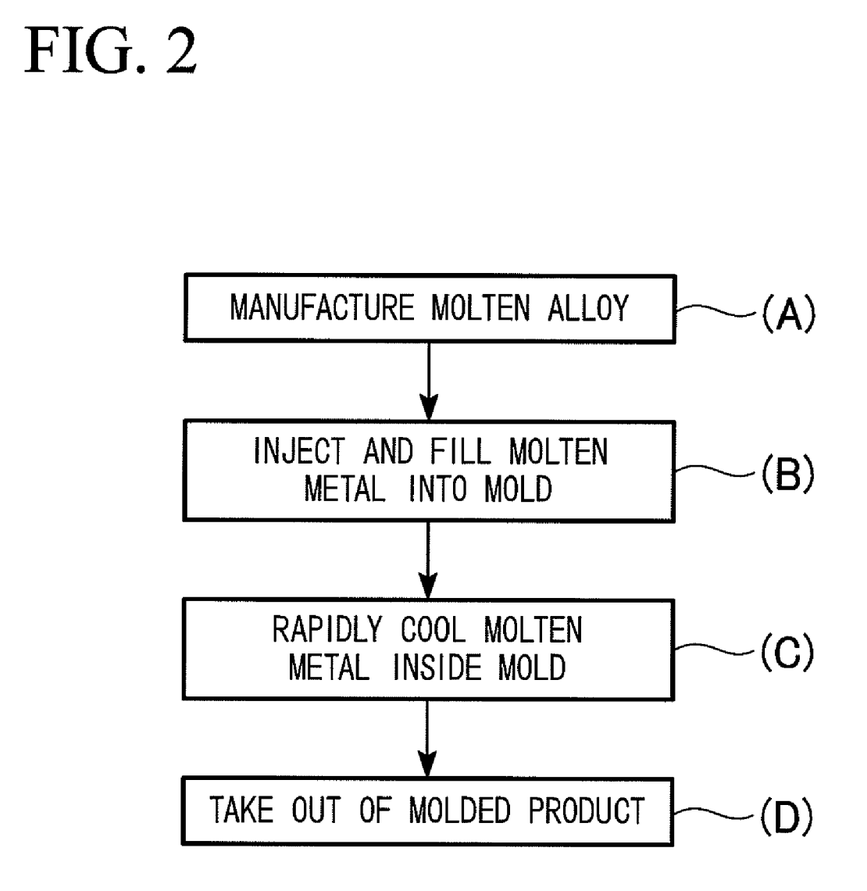
FIG. 2 is a process diagram showing an injection molding process of the endoscope lens barrel according to the first embodiment of the present invention.

As shown in FIG. 2, the injection molding includes a process (A) of manufacturing molten metal materials, a process (B) of injecting and filling the molten metal into a mold, a process (C) of rapidly cooling the molten metal in the mold to obtain a non-crystalline alloy (metal glass) having a glass transition area of 20° C. or more, and a process (D) of taking a rough product out of the molded product obtained by rapidly cooling the molten metal.

First, in the process (A), the molten metal is manufactured by heating and melting the Zr-based alloy. Subsequently, in the process (B), the molten metal is injected and filled into the mold. A known injection molding machine may be used for the injecting-filling operation.

Subsequently, in the process (C), the molten metal is solidified in a non-crystalline state by rapidly cooling the molten metal and the mold at 10° C./sec or more so as to obtain metal glass, and the rough product of the endoscope lens barrel 10 is formed. For the rapid cooling operation, for example, ultra-rapid cooling solidification or the like may be used. In addition, when the cooling operation of the molten metal is performed at the temperature less than 10° C./sec in the process (C), the non-crystallization of the molten metal does not occur, and the non-crystalline molded product cannot be obtained.

Subsequently, in the process (D), the rough product is taken out from the mold. Then, the rough product is subjected to a secondary process such as deburring and cutting of the lens barrel fixing screw hole 11 and the groove 15, thereby obtaining the endoscope lens barrel (molded product) 10. It is desirable that the secondary process be performed in the state where the rough product of the molded product is maintained at a temperature not exceeding the crystallization temperature (about 490° C.) of the Zr-based alloy.

Accordingly, it is possible to prevent the metal material from being crystallized by the heat of the secondary process, and thus to obtain a non-crystalline molded product.

In addition, in the process (B) of performing the injecting-molding operation, it is desirable that a centrifugal force be applied so that the mold is rotated at a speed equal to or greater than 1000 and equal to or lower than 5000 rpm by a rotation mechanism provided in the mold. Accordingly, it is possible to remove from the molten metal gas components such as air mixed into molten metal, and thus to improve the filling rate at which the mold is filled with the molten metal. Therefore, it is possible to obtain the high-quality molded product without air holes. In addition, the injection molding performed by applying a centrifugal force is limited to the mold having a size rotatable by the rotation mechanism, and is particularly applied to small components such as an endoscope lens barrel having a small mold dimension. In the case where the mold dimension is small, it is desirable that the rpm of the mold be equal to or greater than 4000 and equal to or less than 5000 rpm in order to obtain an effective centrifugal force.

Since the endoscope lens barrel (molded product) 10 manufactured as described above exhibits a low Young's modulus/high strength as properties of the metal glass included in the Zr-based alloy, the endoscope lens barrel has excellent mechanical strength and durability. For this reason, the endoscope lens barrel is hardly deformed.

In addition, since the metal glass can be subjected to the injection molding, and does not cause solidification shrinkage differently from the crystalline metal, the metal glass exhibits excellent transferability with respect to the mold. Accordingly, the molded product of the present invention obtained by using the metal glass has excellent accuracy of dimension. For this reason, it is possible to decrease the number of secondary processes after the injection molding, and thus to improve productivity. In addition, since the endoscope lens barrel 10 of the embodiment is manufactured by using the Zr-based alloy which has particularly excellent thermo-moldability from amongst the metal glasses, the endoscope lens barrel has particularly excellent accuracy of dimension.

As described above, since the endoscope lens barrel 10 is manufactured by injecting-molding the metal glass having excellent strength, durability, and accuracy of dimension, the endoscope lens barrel has excellent strength, durability, and accuracy of dimension regardless of a small complex shape having a hollow portion thereof, and is hardly deformed even in the application of an external force. For this reason, in the endoscope lens barrel 10, it is possible to accurately fix the optical element to a desired position of the hollow portion (the illumination hole 12 and the imaging hole 16). In addition, the deviation of the optical axis of the optical element fixed to the endoscope lens barrel 10 hardly occurs during a long period of time.

Next, an embodiment of the imaging unit 30 in which various optical elements are fixed to the endoscope lens barrel 10 will be described with reference to FIGS. 3A to 6.

Figure 3A:
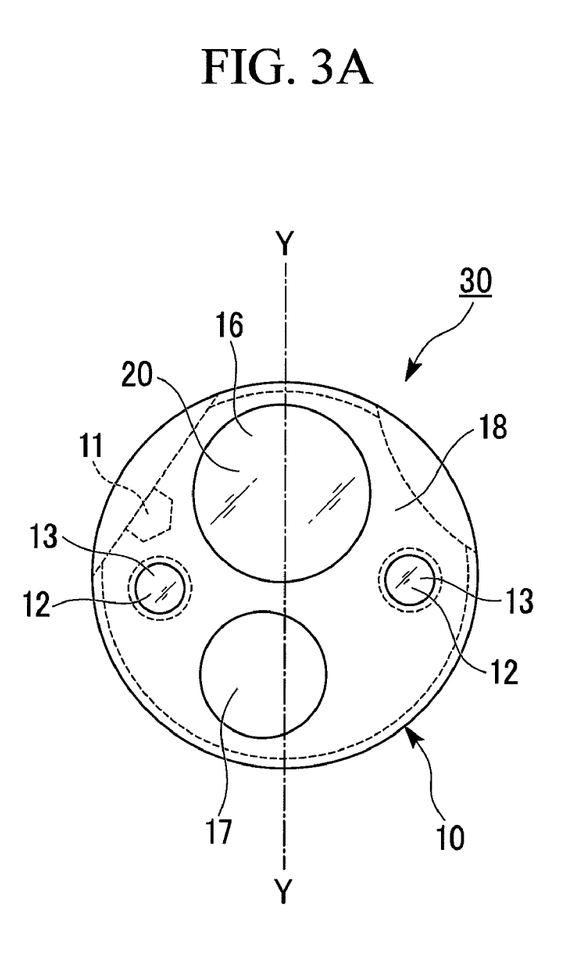
FIG. 3A is a front view showing an imaging unit according to the first embodiment of the present invention.
Figure 3B:
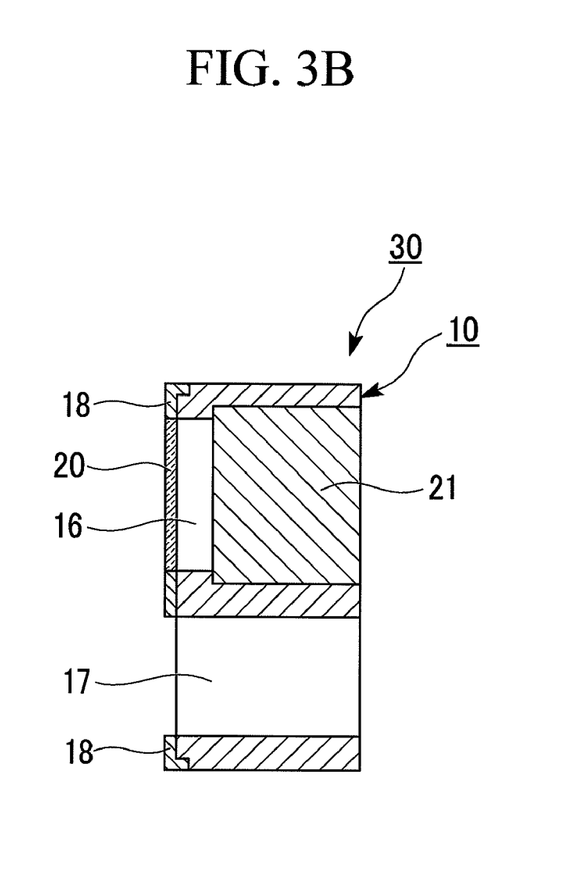
FIG. 3B is a sectional view taken along the line Y-Y of FIG. 3A and showing the imaging unit according to the first embodiment of the present invention.

As shown in FIG. 3A, the imaging unit 30 includes the endoscope lens barrel 10 which is provided in the front end of the imaging unit 30, an imaging unit cover 18 which is fixed to the front surface of the endoscope lens barrel 10, an object lens (optical element) 20 which is fixed so as to close the channel of the imaging hole 16, and an illumination lens (optical element) 13 which is fixed to the illumination hole 12. In addition, as shown in FIG. 3B, an imaging element (optical element) 21 such as a CCD and a CMOS is fixed to the inside of the imaging hole 16. Further, a transmission cable (not shown) extends from the imaging element 21 so as to transmit a video to a monitor or a recording device.

Figure 4:
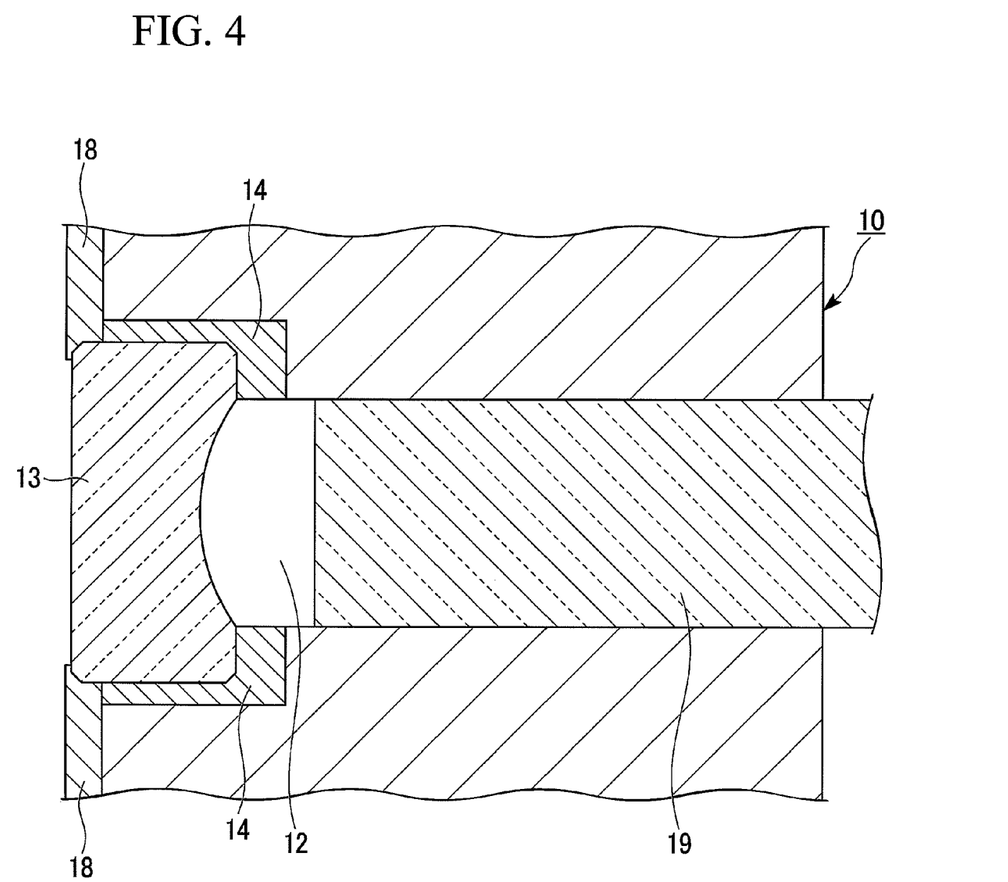
FIG. 4 is a partially sectional view showing the periphery of a bonding portion between an optical element (an optical fiber and an illumination lens) and the endoscope lens barrel of the imaging unit according to the first embodiment of the present invention.

As shown in FIG. 4, an optical fiber (optical element) 19 is fixed to the inside of the illumination hole 12, and is drawn out the outside of the illumination hole 12 from the end opposite to the fixed portion of the illumination lens 13. The front end of the optical fiber 19 drawn out to the outside of the illumination hole 12 is provided with a light source (not shown).

As shown in FIG. 4, the illumination lens 13 is fixed to one end of the illumination hole 12 through solder 14 melted at a temperature of 380° C. which is lower than the glass transition temperature (about 400° C.) of the Zr-based alloy forming the endoscope lens barrel 10.

Since the illumination lens 13 is fixed through the solder 14 melted at a temperature less than the glass transition temperature of the non-crystalline alloy, even when the heat of the solder-bonding operation is applied to the endoscope lens barrel 10, it is possible to make the deterioration of the shape stability of the endoscope lens barrel 10 difficult. More desirably, as in the example of the embodiment, it is desirable to provide a certain degree of temperature gap between the melting temperature of the solder 14 and the glass transition temperature of the Zr-based alloy. Accordingly, it is possible to make the deterioration of the shape stability of the endoscope lens barrel 10 caused by the heat of the solder-bonding operation difficult.

Incidentally, in general, the material of the optical element fixed to the endoscope lens barrel (molded product) has a linear expansion coefficient of 8 to $10 \times 10^{-6}/°$ C. In addition, as the linear expansion coefficient of the molded product is close to that of the optical element, it is possible to largely alleviate the residual stress applied to the optical element. In detail, when the linear expansion coefficient of the molded product is $15 \times 10^{-6}/°$ C. or less and a ratio of the expansion coefficient (the molded product/the optical element) is 1.5 or less, it is possible to largely alleviate the residual stress applied to the optical element. More desirably, the linear expansion coefficient of the metal glass is 8 to $10 \times 10^{-6°}$ C., which is same as that of the optical element.

In the present invention, since the endoscope lens barrel (molded product) 10 is made from the metal glass having a low expansion property such that the linear expansion coefficient is $15 \times 10^{-6}/°$ C. or less, the endoscope lens barrel has excellent shape stability. For this reason, it is possible to largely alleviate residual stress applied to the optical element, and to cause crack of the optical element difficult.

In the embodiment, the linear expansion coefficient of the endoscope lens barrel 10 is $10 \times 10^{-6}/°$ C., the linear expansion coefficient of the illumination lens 13 is $8.5 \times 10^{-6}/°$ C., and the ratio of the expansion coefficient between the endoscope lens barrel 10 and the illumination lens 13 is about 1.17. For this reason, even when the illumination lens 13 is solder-bonded to the endoscope lens barrel 10, the possibility of cracking of the illumination lens is extremely small.

Figure 5A:
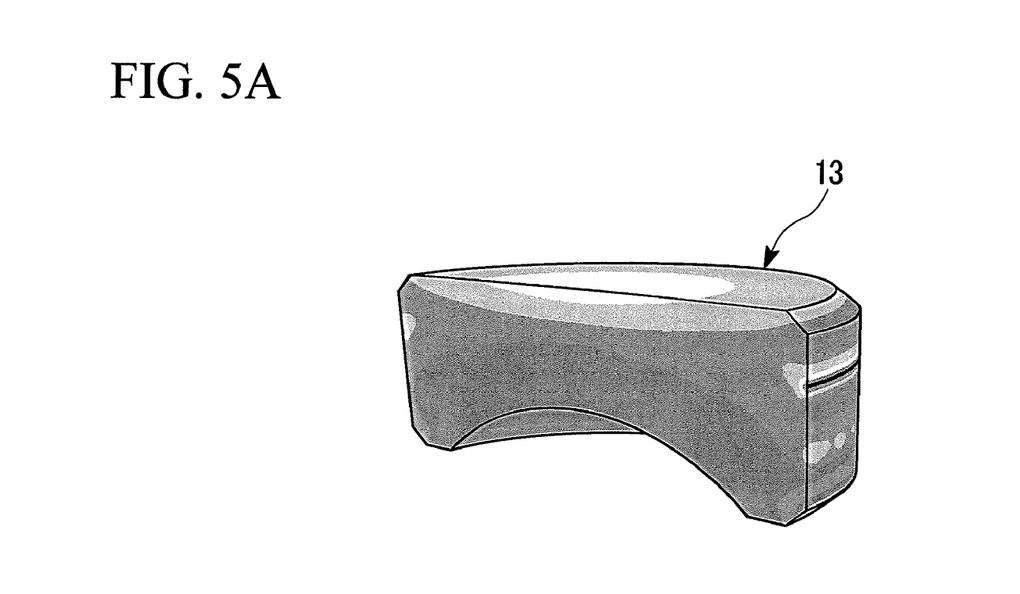
FIG. 5A is a simulation diagram showing residual stress of the optical element (the illumination lens) solder-bonded to the endoscope lens barrel according to the first embodiment of the present invention.
Figure 5B:
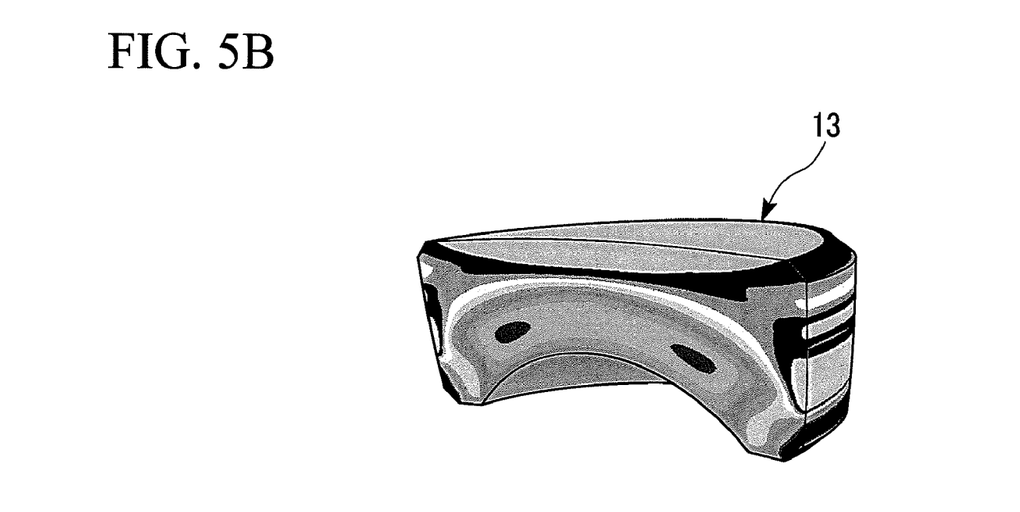
FIG. 5B is a simulation diagram showing residual stress of the optical element (the illumination lens) bonded to the conventional stainless steel lens barrel.

Here, residual stress applied to the illumination lens 13 upon solder-bonding the illumination lens 13 to the endoscope lens barrel 10 is shown in FIG. 5A. In addition, the residual stress applied to the illumination lens 13 upon solder-bonding the illumination lens 13 to the conventional stainless steel lens barrel is shown in FIG. 5B. In FIGS. 5A and 5B, the portion applied with the strong residual stress is depicted by the strong contrasting density. Since the linear expansion coefficient of the endoscope lens barrel 10 is $10 \times 10^{-6}/°$ C. as described above, the residual stress applied to the illumination lens 13 shown in FIG. 5A is small. Meanwhile, it is understood that the linear expansion coefficient of stainless steel is $17 \times 10^{-6}/°$ C., and strong residual stress is applied to a large area of the illumination lens 13 as shown in FIG. 5B.

The Zr-based alloy used in the endoscope lens barrel 10 is the non-crystalline alloy. Since the non-crystalline does not have a crystal grain boundary of general crystalline metal, and does not cause grain-boundary corrosion, the non-crystalline alloy exhibits excellent corrosion resistance. Since the endoscope lens barrel 10 is provided in the front end of the imaging unit 30, the endoscope lens barrel is exposed to various sterilization/pasteurization processes used to clean the medical endoscope. However, since the non-crystalline alloy has the above-described properties, the non-crystalline alloy has excellent corrosion resistance against these processes. Accordingly, in the imaging unit 30 using the endoscope lens barrel 10, the deformation and deterioration hardly occur in the imaging unit even after long-term use, and the deviation of the optical axis of the optical element hardly occurs.

In addition, regarding the corrosion resistance of the endoscope lens barrel 10, the sterilization/pasteurization processes are performed on the endoscope, and a variation in the weight, X-ray diffraction, and corrosion and deterioration were measured. However, the weight of the endoscope lens barrel 10 is not changed, and the crystallization and the corrosion and deterioration of the endoscope lens barrel 10 were not observed. On the basis of the result, it is proved that the endoscope lens barrel 10 has excellent corrosion resistance. In addition, as the sterilization/pasteurization processes, a povidone iodine solution immersion process, a high-temperature-pressure pasteurization process, a glutaraldehyde solution immersion process, an EOG (ethylene oxide gas) pasteurization process, and a hydrogen peroxide gas pasteurization process were performed.

In addition, the endoscope lens barrel 10 has excellent durability against an oil or a saline solution as a usage environment of the industrial endoscope. The endoscope lens barrel 10 was subjected to an immersion test for 30 days in the environment (medium) normally performed on the industrial endoscope, and a variation in the weight, X-ray diffraction, and corrosion and deterioration were measured. However, the weight of the endoscope lens barrel 10 changed little before and after the test, and the crystallization or corrosion and deterioration of the endoscope lens barrel 10 were not confirmed. In SUS303 (stainless steel) as a comparative sample subjected to the immersion test, corrosion was confirmed in the immersion test of a saline solution. Accordingly, it is possible to determine that the endoscope lens barrel 10 has excellent corrosion resistance. In addition, as the medium of the immersion test, oil such as diesel oil and machine oil, a 5% saline solution, and the like may be exemplified.

Further, when the imaging unit cover 18 is made from the metal glass as in the endoscope lens barrel 10, it is possible to improve abrasion resistance and mechanical strength thereof. Accordingly, in the case of the test of a metal component such as a mold, it is possible to improve the durability of the imaging unit.

Second Embodiment

Next, a compact camera lens barrel (not shown) as a second embodiment of the present invention will be described.

The compact camera lens barrel according to the embodiment is manufactured in accordance with the same method as the first embodiment by using Zr-based alloy (a crystallization temperature: about 490° C., a glass transition temperature: about 350° C., and a glass transition area: about 140° C. or more) having a composition of $Zr_{50}Cu_{17.5}Al_{7.5}Ni_{10}Ti_5Be_{10}$. The shape of the compact camera lens barrel is the shape of the general camera lens barrel. As in the above-described embodiment, the compact camera lens barrel of the example of the embodiment has satisfactory transferability with respect to the mold, and has excellent accuracy of dimension equal to that of the compact camera lens barrel using a resin material. In addition, regarding the manufacture of the compact camera lens barrel, when a secondary process such as deburring or cutting is performed on a rough product of the compact camera lens barrel obtained by the injection molding so as to form a hole and/or a groove therein, as in the first embodiment, crystallization of the metal glass can be prevented by maintaining the temperature of the rough product so that the temperature thereof does not exceed the crystallization temperature (about 490° C.) of the Zr-based alloy.

Figure 6:
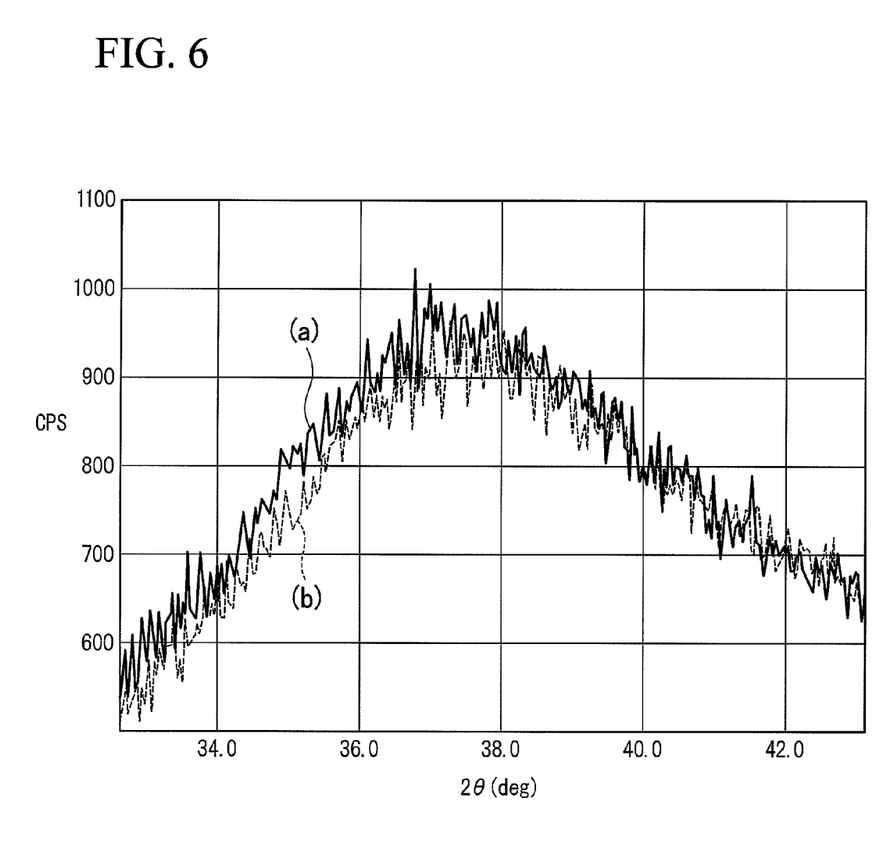
FIG. 6 is a graph (the vertical axis: the diffraction intensity (CPS), and the horizontal axis: the diffraction angle ($2\theta$ (deg)) showing a measurement result in which a variation in the non-crystalline state is measured by the X-ray diffraction before and after a secondary process for a compact camera lens barrel according to a second embodiment of the invention.

Here, regarding the crystallization due to the secondary process, the measurement result of the diffraction of the compact camera lens barrel obtained through the X-ray diffraction measurement method is shown in FIG. 6. FIG. 6A shows the diffraction result of the compact camera lens barrel before the secondary process, and FIG. 6B shows the diffraction result of the compact camera lens barrel after the second process. There was almost no difference between FIGS. 6A and 6B. In addition, the peculiar peak of the crystalline metal was not observed in the graph of FIG. 6. Therefore, the compact camera lens barrel can be maintained in the non-crystalline state without being crystallized by the heat of the secondary process.

As in the above-described embodiment, since the compact camera lens barrel uses the Zr-based alloy having a linear expansion coefficient substantially equal to that of the optical element, the compact camera lens barrel has excellent shape stability. For this reason, even when a heat history of 100° C. within the heatproof temperature of adhesive occurs in the compact camera lens barrel after fixing the optical element to the compact camera lens barrel, cracking of the optical element or deciduation of the optical element from the lens barrel hardly occur. In addition, the compact camera lens barrel has excellent strength and durability as in the molded product of the above-described embodiment. Accordingly, since the compact camera lens barrel is provided in the front end of the imaging unit, even when the compact camera lens barrel is influenced by an external force, it is possible to maintain high strength and durability.

The technical scope of the present invention is not limited to the above-described embodiments, but various modifications can be made thereto within the scope not departing from the spirit of the present invention. For example, in the above-described embodiments, the Zr-based alloy is used as the metal material, but the present invention is not limited thereto. For example, a Fe-based alloy, Ti-based alloy, Mg-based alloy, and the like may be used in addition to the Zr-based alloy shown in the embodiments if those metal materials can form non-crystalline alloy (metal glass) having a linear expansion coefficient of $15 \times 10^{-6}/°$ C. or less and a glass transition area of 20° C. or more, and can allow the molded product to have excellent strength, durability, accuracy of dimension, shape stability, and productivity. In addition, the optical element fixing component is not limited to the lens barrel of the above-described embodiments, but may be other components.

As described above in detail, the optical element fixing component of the present invention is made from the non-crystalline alloy (metal glass) having excellent thermo-moldability, excellent strength, excellent corrosion resistance, and a low linear expansion coefficient of $15 \times 10^{-6}/°$ C. or less and a glass transition area of 20° C. or more, the optical element fixing component has excellent strength, durability, corrosion resistance, accuracy of dimension, shape stability, and productivity. In addition, since the imaging unit in which the optical element is fixed to the optical element fixing component of the present invention has excellent strength, durability, corrosion resistance, and shape stability, deviation of the optical axis of the optical element, cracking or deciduation thereof hardly occur.

According to the present invention, it is possible to obtain an optical element fixing component having excellent strength, durability, corrosion resistance, accuracy of dimensionaccuracy of dimension, shape stability, and productivity. Also, according to the present invention, it is possible to obtain an imaging unit having excellent strength, durability, corrosion resistance, accuracy of dimensionaccuracy of dimension, and shape stability and hardly causing the deviation of the optical axis of the optical element, breakage or deciduation thereof.

What is claimed is:

1. An optical element fixing component having a hollow portion in which an optical element is provided therein,
   wherein the optical element fixing component is made from a metal glass non-crystalline alloy, and a ratio of a linear expansion coefficient of the optical element fixing component toward a linear expansion coefficient of the optical element is 1.5 or less.

2. The optical element fixing component according to claim 1, wherein the ratio is 1.0 or more.

3. The optical element fixing component according to claim 1, wherein the linear expansion coefficient of the metal glass non-crystalline alloy is $15 \times 10^{-6}/°$ C. or less.

4. The optical element fixing component according to claim 1, wherein a glass transition area of the metal glass non-crystalline alloy is 20° C. or more.

5. The optical element fixing component according to claim 1, wherein the metal glass non-crystalline alloy is a Zr-based alloy.

6. An imaging unit comprising:
   the optical element fixing component according to claim 1; and
   an optical element which is fixed to a hollow portion of the optical element fixing component.

7. The imaging unit according to claim 6, further comprising a protection cover which is made from a metal glass non-crystalline alloy.

8. The imaging unit according to claim 6, further comprising a bonding layer formed by a melted bonding material provided between the optical element fixing component and the optical element.

9. The imaging unit according to claim 8, wherein a melting temperature of the bonding material is lower than a glass transition temperature of the metal glass non-crystalline alloy.

10. An endoscope apparatus comprising the imaging unit according to claim 6.

11. A camera comprising the imaging unit according to claim 6.

* * * * *